United States Patent [19]

Lester

[11] 4,151,831
[45] May 1, 1979

[54] FERTILITY INDICATOR

[75] Inventor: Robert W. Lester, Manhasset, N.Y.

[73] Assignee: Safetime Monitors, Inc., New York, N.Y.

[21] Appl. No.: 741,596

[22] Filed: Nov. 15, 1976

[51] Int. Cl.² ............................................. A61B 5/00
[52] U.S. Cl. .................................. 128/736; 128/738; 58/4 M; 58/152 B; 364/415
[58] Field of Search ................ 128/2 H, 2.05 R, 2 R; 235/92 MT, 92 T, 85 FC; 58/4 M, 152 A–152 B; 73/362 R; 364/417, 557

[56] References Cited

U.S. PATENT DOCUMENTS

| | | | |
|---|---|---|---|
| 3,031,654 | 4/1962 | Galen | 58/4 M |
| 3,152,437 | 10/1964 | Vasselli | 58/4 M |
| 3,472,018 | 10/1969 | Papworth | 58/4 M |
| 3,572,316 | 3/1971 | Vogelman et al. | 128/2.05 R |
| 3,872,726 | 3/1975 | Kauffeld et al. | 235/92 MT X |
| 3,910,257 | 10/1975 | Fletcher et al. | 128/2 H X |
| 3,937,004 | 2/1976 | Natori et al. | 58/152 A X |
| 3,940,595 | 2/1976 | Turner | 235/92 MT X |
| 3,940,742 | 2/1976 | Hudspeth et al. | 128/2 H X |
| 3,979,056 | 9/1976 | Barnes | 235/92 MT |
| 4,031,365 | 6/1977 | Raggiotti et al. | 235/92 MT X |
| 4,074,516 | 2/1978 | Kondo | 58/152 B |

*Primary Examiner*—Robert W. Michell
*Assistant Examiner*—Francis J. Jaworski
*Attorney, Agent, or Firm*—Allison C. Collard; Thomas M. Galgano

[57] ABSTRACT

A fertility indicator for measuring and detecting the body temperature of a human subject over a menstrual cycle having a timer for generating time based signals, and a logic circuit connected to the clock timer and being responsive to the time based signals for selecting the proper combinations of the time based signals and for indicating the correct present time. There is a temperature sensor coupled to the logic circuit for measuring the body temperature of the human subject. A solid state memory circuit having coded information command signals is coupled to the logic circuit for sequencing the logic circuit to take a plurality of temperature readings at a preset real time and to terminate the readings when the temperature has stabilized. A data storage circuit is provided for sequentially recording each of the stabilized temperatures that were measured, and a display circuit responsive to the solid state memory and data storage circuits, indicates the status of fertility of the subject during a menstrual cycle. There is also an alarm circuit coupled to the logic circuit and it has a variable pitch responsive to the solid state memory circuit for indicating the time when the subject's temperature has to be taken. Lights or words can indicate user's status.

14 Claims, 11 Drawing Figures

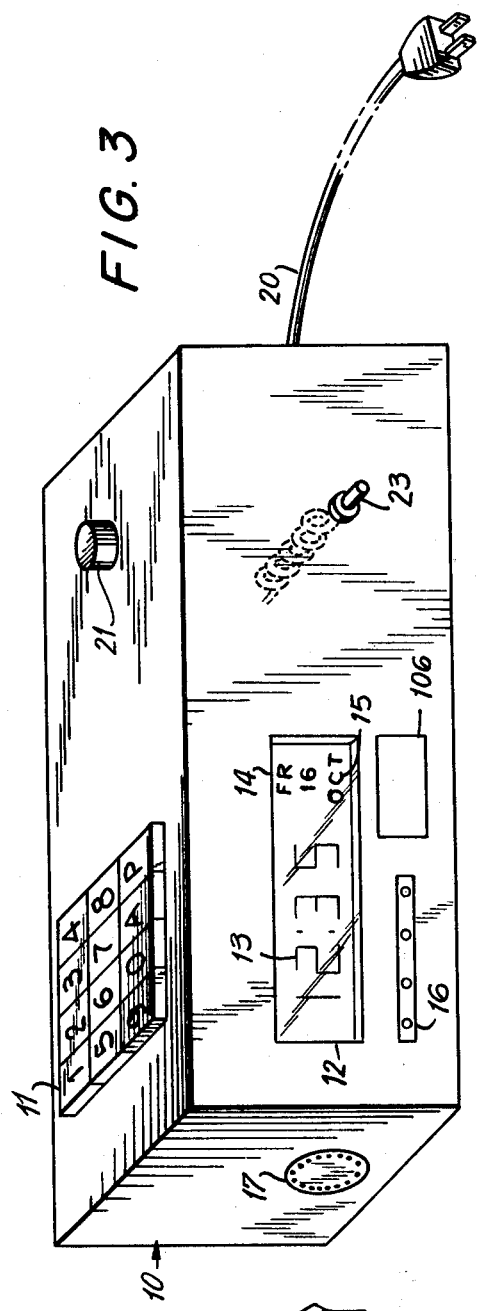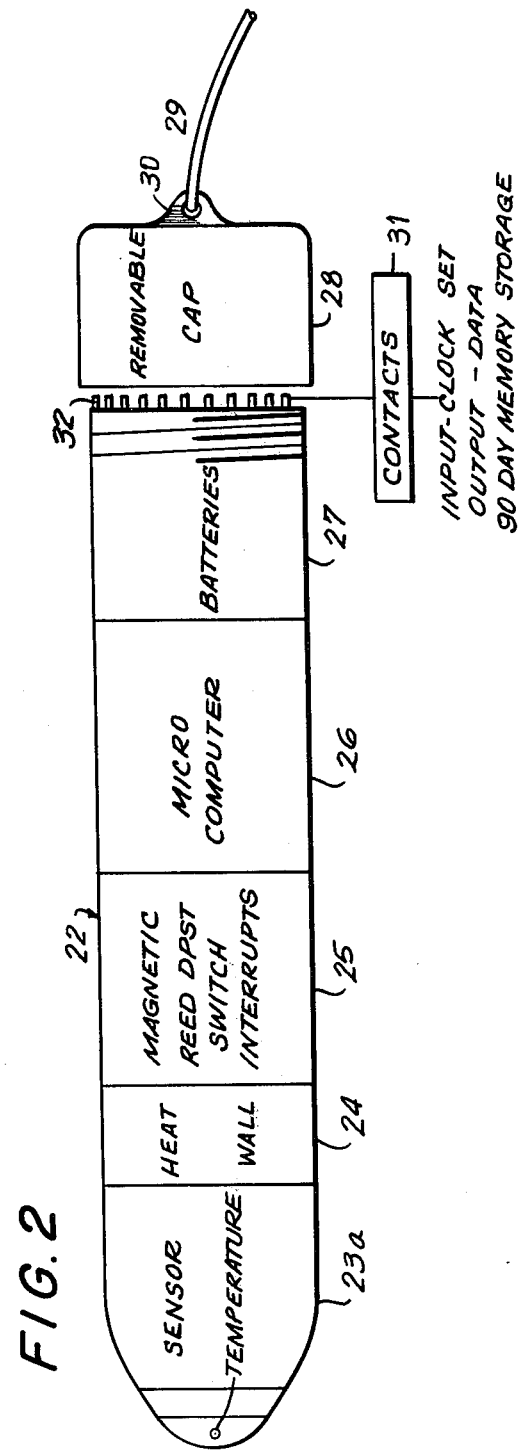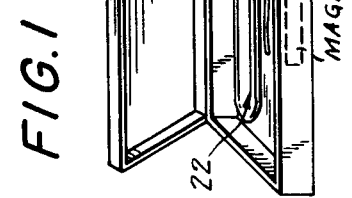

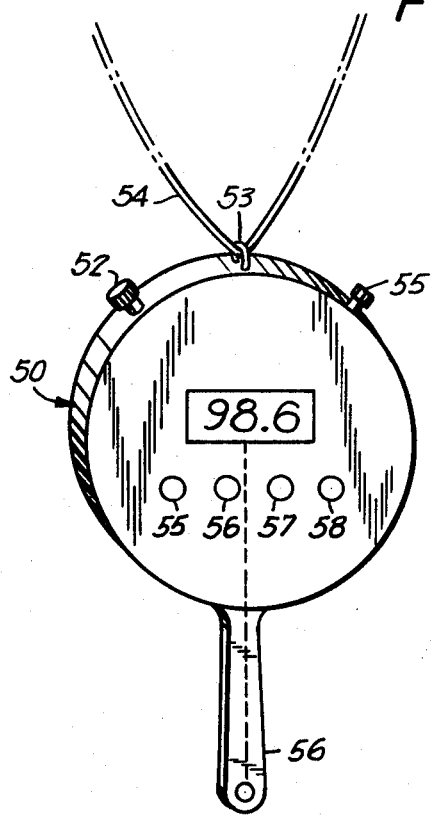
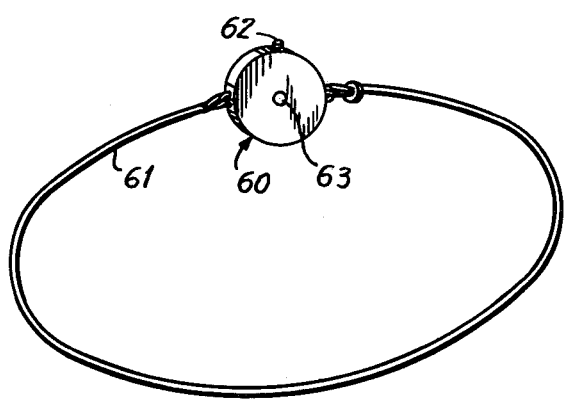
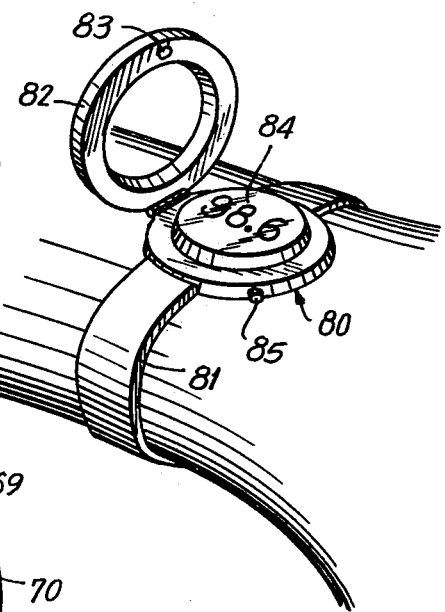
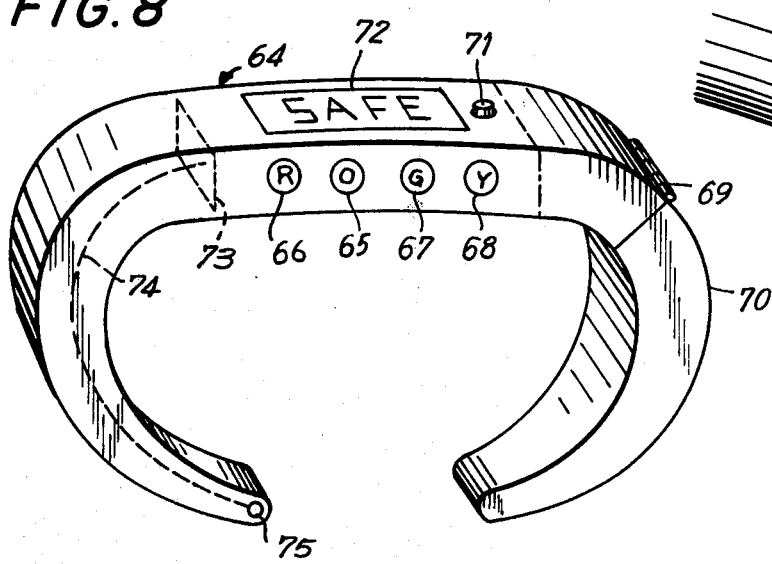

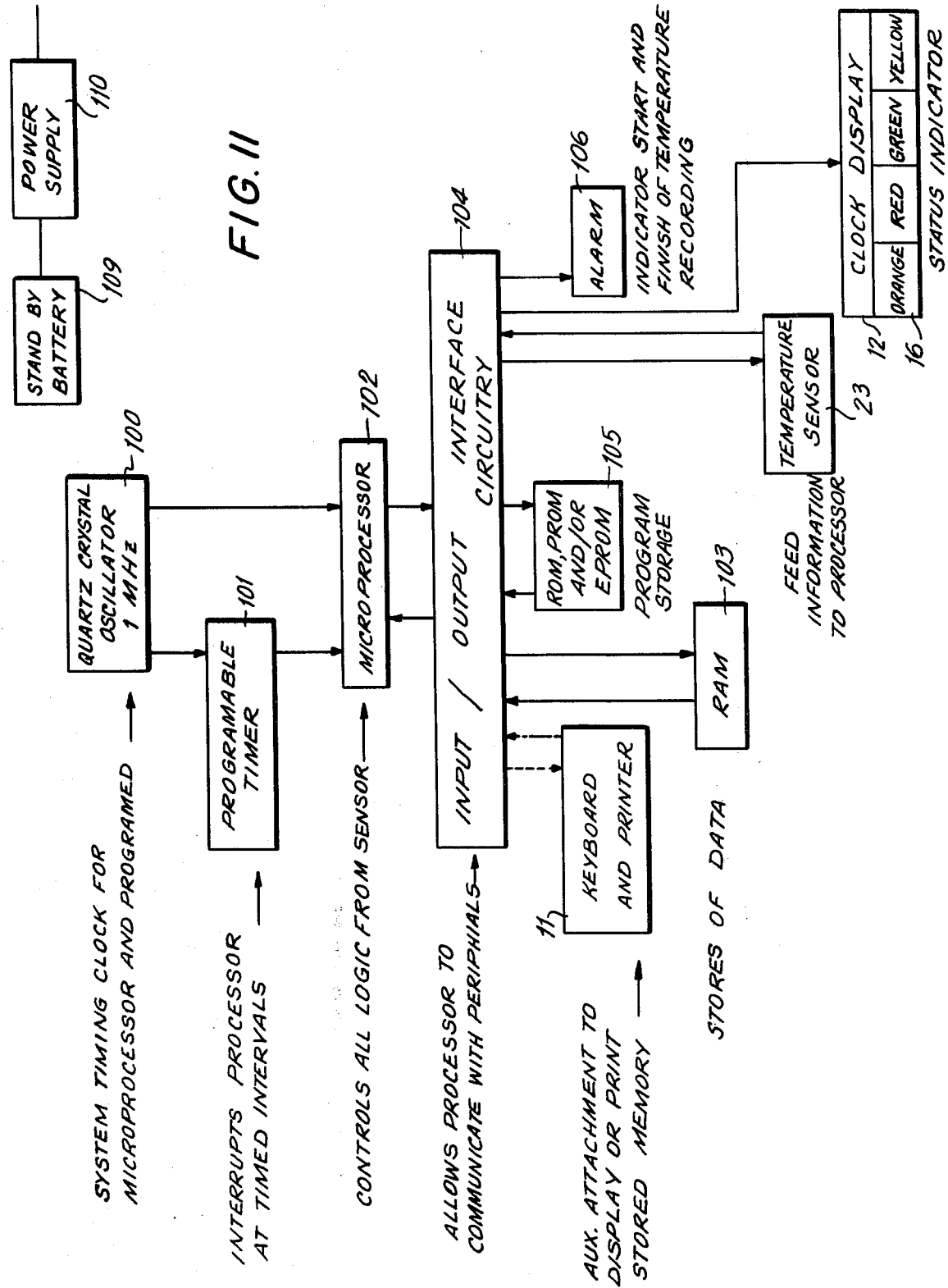

FERTILITY INDICATOR

The present invention relates to an electronic fertility indicator for detecting and recording the status of a womens menstrual cycle.

Despite the advances of modern medicine, the only method of birth control which is completely safe and completely effective is complete sexual abstinence. Only in the last half century has knowledge of female reproductive physiology been systematically applied to the development of a technique for birth control in which sexual abstinence is timed to coincide with the fertile phase of the woman's menstrual cycle. Variously referred to as rhythm, or the safe period, this method usually requires that couples abstain from intercourse for at least eight days approximately at midcycle between the menses under this system. It was though that ovulation, or release of the ovum from the ovary, occurred once per cycle; that the ovum was susceptible to fertilization for only 24 hours; and that the sperm deposited in the female reproductive tract was capable of fertilizing the ovum for only about 72 hours. Thus, if intercourse did not occur just before and during this period, the sperm could not fertilize the ovum and conception could not take place. This in theory, is a safe and simple method of birth control.

The difficulty in practicing rhythm is that ovulation normally occurs about 14 days prior to the next menstrual period but not necessarily 14 days after the previous menstrual period. Different techniques have been devised for predicting ovulation in advance or for identifyng its occurrence immediately afterwards, but each raises different problems and no method is universally applicable. If all women had regular menstrual cycles, calendar rhythm would be reliable. They could readily known on a calendar the safe days after and before ovulation and restrict intercourse accordingly. But cycles vary by an average of about 7 to 13 days for the peak reproductive years and by even greater margins for girls in their teens and women approaching menopause. For those women desiring to become pregnant, they can also never be sure of ovulation time best for intercourse. Temperature rhythm relies on changes in basal body temperature (BBT) to identify the time of ovulation. A rise of about 0.3° to 0.5° Centigrade, or 0.5° to 1.0° Fahrenheit, occurs in the basal body temperature at about the time of ovulation. The effectiveness of temperature rhythm depends on how carefully the temperature is recorded, and how well this temperature correlates with the actual time of ovulation. Then if intercourse is avoided until three days after this temperature rise and takes place only during the remaining ten to twelve days before the menses, there is no likelihood of pregnancy.

Unlike the calendar method, which depends primarily on the regularity of the menstrual cycle, the thermal or temperature method depends upon identification of a single event—the rise in basal body temperature (BBT). This occurs at the time of ovulation as a result of the elevated progesterone level. The basal body temperature refers to the temperature of the body at complete rest.

The rise in BBT is small, only about 0.5° to 1.0° Fahrenheit (0.3° to 0.5° Centigrade). In most cases it is abrupt but sometimes takes as long as four or five days to stabilize. If fertilization does not take place, the corpus luteum ceases to function, after approximately 13 to 16 days, production of the hormone progesterone, which caused the temperature to rise initially, decreases and BBT falls.

Success in avoiding pregnancy with the BBT method depends on how accurately the temperature is taken and recorded and how well the shift correlates with ovulation.

Because it is the shift in temperature rather than the temperature itself which must be noted, the readings must be taken daily and always at the same time. Ideally, the temperature should be taken in the morning while still in bed after at least five hours of uninterrupted sleep and before eating, drinking, or extended conversation, since any activity at all can raise BBT. Temperature readings may be taken either orally, rectally, or vaginally as long as the same method is always used.

The major drawback of the temperature measuring method is readily apparent. It cannot predict in advance when ovulation will take place.

The fertility indicator of the present invention is an electronic instrument intended to record at a specific time of day the minimum or maximum temperature of the patient's body. Multiple readings on subsequent days will be stored in the indicator's memory for later readout, which will demonstrate the existence of a biphasic curve or the absence of one.

The inventive fertility indicator, with its extraordinarily accurate temperature readings and completely accurate memory and readout, will eliminate these common difficulties of conventional birth control methods. In the interest of obtaining the most readings of basal body temperature, the fertility indicator has been designed in one embodiment for insertion into the vagina where body temperature fluctuations will be accurately reflected.

The vagina as a location is anatomically sound and psychologically appropriate. In this embodiment, the size of the fertility indicator is similar to the commonly used vaginal tampons and the attached string. It is designed after the fashion of the tampon, and provides an ease of insertion and removal, in a manner already understood by the majority of patients. The program for use calls for insertion of the fertility indicator at bedtime and its removal on awakening.

The fertility indicator (when used as a vaginal tampon) will record the temperature at a specific time, for example, 5:00 AM which will be consistent throughout the period of observation. If the fertility indicator is not within the vagina at the time of recording, this will be obvious on the temperature recorded. The patient need only keep a sequential record of unusual influences on basal body temperature such as: fever, late night activity, early rising, etc.

The fertility indicator of the present invention is a microprocessor based thermometer capable of sensing and recording temperature to an accuracy of 1/20° F. within a range of 90°–110° F. The device can be packaged in the form of a table top version or a wrist watch or necklace version which includes a digital LED display calendar, alarm and time read-out, and also a fever indicator for general purposes. When the temperature is to be taken at a predetermined set time, an alarm on the device will sound alerting the person to apply one of the temperature sensing devices to the body to begin the temperature reading. After a predetermined set interval and after the temperature has risen and stabilized, it is recorded in a program storage unit which keeps a record of each of the basal body temperatures over a period of the last month or year. In a typical fertility cycle, the apparatus of the invention provides a red LED lamp to go on if the temperature sensing device notes a decrease in temperature, such as when menstruation has occurred or just after its occurrence. The red light will stay on for a period of five or six days while the temperature is low. A yellow lamp is provided to indicate to the user an increase in the basal body temperature and thereby denoting ovulation has occurred. The yellow lamp is programmed to remain on for forty-eight hours and then goes off. A green lamp is then programmed to go on automatically and stay on until menstruation occurs and then goes off because of the temperature decrease. If the green lamp stays on for more than twenty-one days, an orange lamp will be turned on simultaneously to indicate a high degree of the possibility of pregnancy suggesting that the user check with her doctor. The orange lamp will remain on until there is a change in the status of the user. After repreated uses of the apparatus of the invention, several months of fertility data are stored and can be read out on a printer or other type of display for comparison. Moreover, the device of the invention can be used to predict the date of ovulation and fertility time once a pattern is established and thus turn on the yellow warning light two or three days in advance of ovulation as a safeguard against unwanted conception.

It is therefore, an object of the present invention to provide a fertility indicator having a program storage capability for predicting and indicating to the user the fertile periods over a menstrual cycle.

It is another object according to the present invention to provide a fertility indicator which is simple in design, easy to utilize and reliable in operation.

Other objects and features of the present invention will become apparent from the following detailed description considered in connection with the accompanying drawings which disclose the embodiments of the invention. It is to be understood, however, that the drawings are designed for the purpose of illustration only and not as a definition of the limits or scope of the invention.

In the drawings, wherein similar reference characters denote similar elements throughout the several views:

FIG. 1 discloses a container for storing and deactivating one type of temperature sensing probe according to the invention;

FIG. 2 is a plan detailed view of the probe of FIG. 1;

FIG. 3 is a temperature indicator and recorder;

FIG. 6 is a further embodiment of the invention in the form of a pendant to be worn around the neck of the user for daily temperature measurements;

FIG. 7 is a further embodiment of the invention in the form of a waist worn temperature sensing device;

FIG. 8 is a further embodiment of the invention using a wrist watch as the temperature sensing device;

FIG. 9 is another embodiment using the hinged cover of a watch case as a temperature sensing element;

FIG. 11 is an electronic software flow chart of the complete fertility indicator according to the invention.

Figures 4, 5:
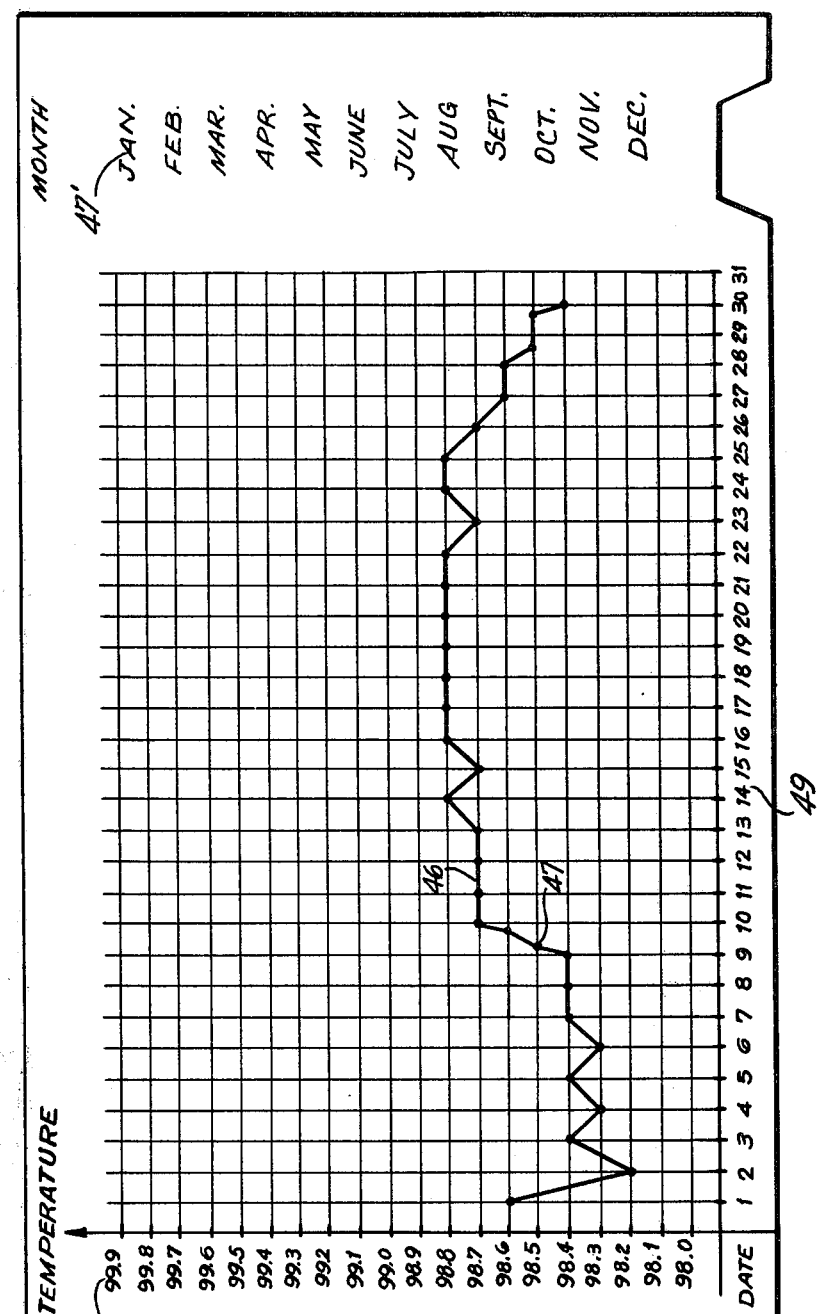
FIG. 4 is a card printer and reader.
FIG. 5 is a chart of temperature against time printed on a card to receive the information from the device of FIG. 4.

Referring to FIGS. 1-3, there is a shown a recording unit 10 having a digital keyboard 11 with a digital clock 12 having LED digital numbers 13 and calendar references for days 14 and months 15 on the front side thereof. Four indicator lights 16 of different colors are also mounted adjacent to the clock. A multi-pin electrical socket 17 is mounted on one side of unit 10, and an electrical line 20 is provided to connect to any conventional power source. Unit 10 also includes a temperature sensing probe 23 electrically connected to unit 10 through a flexible coiled connection wire 19 as shown in broken line. Temperature sensor 23 is designed to be put into the mouth of the user for taking oral temperature readings.

The device of FIG. 2 discloses a vaginal temperature sensor which can be worn by the woman as a tampon and includes a temperature sensor 23, a heat wall 24 and a magnetically operated reed double pole single throw interrupter switch 25. Temperature sensor 23a is connected through the magnetic reed switches to a microcomputer 26 which is prowered by battery 27 for making temperature readings of the basal body temperature. Vaginal temperature probe 22 can operate independently of unit 10 in reading and recording the basal body temperature at preset time intervals while the user is at rest or asleep at predetermined daily timed intervals, such as 5 or 6 a.m. in the morning. The vaginal probe 22 is designed to be worn only at night when temperature readings are to be taken and after a plurality of daily basal body temperatures are taken, the end cap 28 can be removed, and contacts 31 can be connected to a printer or read-out, so that the computer can feed out the stored information into a display. The end of cap 28 includes an eyelet 30 for connection to a tapon-type string 29 to permit easy removal of the probe.

After the probe is removed in the morning following each temperature reading, it is placed into storage box 33. Box 33 has a magnet 34 embedded along one side adjacent to magnetic reed switches 25 so that the electronic circuitry of probe 22 will be disconnected when the probe is placed into the box by the action of the magnet on the reed switches.

With respect to unit 10 of FIG. 3, the user sets the digital clock by means of the twelve pushbuttons on keyboard 11 which includes 0 to 9 plus an AM and PM switch, so that the time can be punched in when the temperature is to be taken. This keyoard gives access only to the address of the clock. Once the fertility device is set and operating and alarm 106 goes off, the user must put the small temperature sensor 23 into her mouth. Once the change of temperature is registered, the microprocessor disables the alarm within five seconds and waits five minutes or as much time as it is programmed for to record the basal body temperature or until temperature levels. The alarm will then reactivate until she removes the temperature sensor from her mouth. Should the sensor accidentally drop out of the user's mouth before the temperature has been recorded, the sensor will note this, causing the alarm to go off again for a new cycle. The embodiment of FIG. 3 requires the user to awaken after a period of rest in response to the alarm, such as at five or six in the morning or just prior to getting up in the morning and inserting the temperature sensor 23 in her mouth until a stabilized temperature reading is taken.

When button 21 is depressed by the user, she can see her temperature displayed at any time until the next twenty-four hour cycle, and an indicator light 16 is also used to advise her of the status in the following order.

A red light will go on after the menstrual period starts. A yellow light will go on when ovulation occurs and stay on forty-eight hours as a safety factor even though ovulation does not last that long. A green light will then go on when the yellow light goes off and stay on until menstruation occurs. The green light will turn off by the temperature drop which occurs during that function. If the green light stays on for more than twenty-one days, a yellow light will also come on at the same time indicating a high possibility of pregnancy. Should the red light remain on for six or more uninterrupted months, it could indicate that menopause has taken place compatible with the age of the woman. This would cause the yellow light to go on with the red light during this period. The yellow light would go on automatically after twenty days if the temperature did not increase. However, in a younger woman, this would normally indicate that she probably has missed her period.

FIG. 4 shows a printer type read-out 40 which can be connected by means of input line 44 to multi-pin socket 17 on the side of unit 10. The printer also has an external power cord for connection to a conventional electrical power source. The printer uses a pre-printed rigid card 42 which is inserted into slot 41. The card as shown in detail in FIG. 5 is a plot of temperature between 98.0° and 99.9° F., and calendar date 49 as well as listing the months 47 along one side of the card. As the date as stored in unit 10 is fed through input line 44, the printer by means of a series of daily dots imprinted onto the card can display the temperature readings which have been recorded and stored over an entire monthly cycle. The doctor can then connect up the dots by means of a line 46 to illustrate the temperature change. The temperature drop between the first and second day as shown in the chart indicates the beginning of menstruation, and a sharp increase in temperature between the ninth and tenth day indicates the beginning of ovulation.

FIG. 6 shows another type of fertility indicator according to the invention consisting of a pendant 50 having LED lamps 55, 56, 57 and 58 consisting of the red, yellow, green and orange lamps in a manner similar to the apparatus of FIG. 3. There is also a temperature indicator 51 which can be turned on by means of depressing button 52. The pendant is meant to hang around the neck of the user by means of a gold chain 54 coupled to hook 53. When the basal body temperature is to be read, the projection 56 of pendant 50 is placed into the mouth of the user underneath her tongue until the temperature has stabilized and can be read. Indicator 51 can also be used to tell the time of day and is adjustable by means of knob 55.

FIG. 7 shows another type of fertility indicator which can be worn by the user around her waist. The temperature sensor can consist of a projection 63 which touches the skin of the user and is mounted on the flat side of indicator 60. An elastic strap 61 connected to both ends of indicator 60 will retain the indicator around the waist of the user. Adjustments are made through knob 62 on one side of the indicator. The user does not have to take her temperature as she would with the watch types.

FIG. 8 discloses another type of fertility indicator in the form of a watch 64 having indicator lamps 65-68 of different colors similar to the embodiment of FIG. 3.

The watch bracelet may include hinge 69 to allow a portion of the bracelet to be opened to insert the watch on the wrist of the user. The watch includes an indicator dial 72 which may include LED read-outs for temperature, time and the condition for fertility. One end of the bracelet includes a temperature sensor 75 connected through conductor 74 to a digital temperature read-out device 73 which may be connected to the microprocessing circuitry of the fertility indicator. A button 71 mounted on the top surface of the watch allows the user to depress the button and make readings of time, temperature or fertility condition. When the user is to take her temperature for the daily reading, she inserts the end of the bracelet containing temperature sensor 75 into her mouth under her tongue until the temperature is stabilized. Watch 64 includes an alarm which will indicate when the temperature cycle has been completed and the temperature sensor can be withdrawn from under the tongue of the user.

In a similar manner, the embodiment of FIG. 9 also includes a temperature sensor 83 in watch 80 which can be lifted up from the surface of the watch for measuring temperature. Sensor 83 is mounted in ring 82 which fits around dial 84 on the wrist of the user. The dial will indicate both temperature and time and can be set by knob 85.

Figure 10:
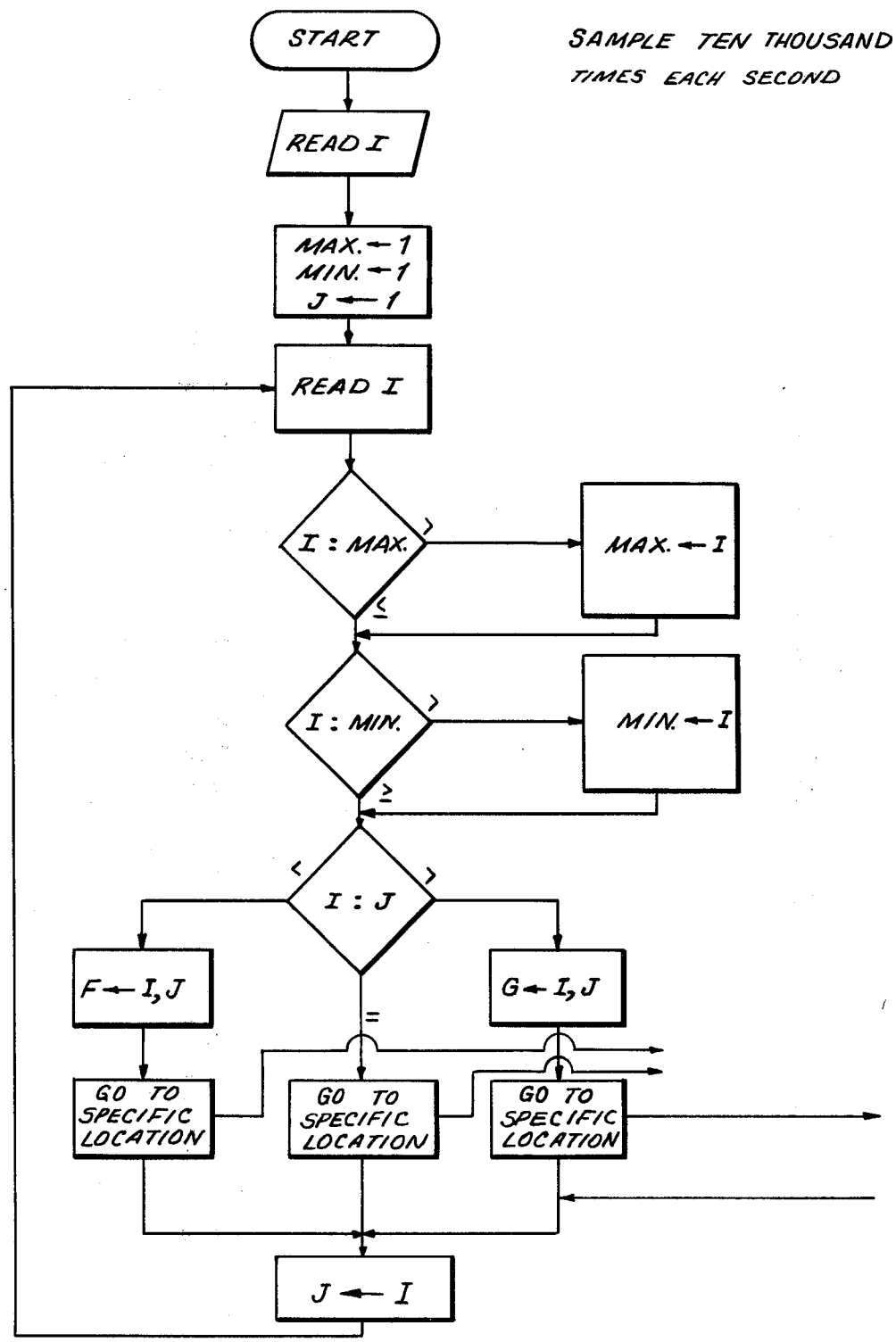
FIG. 10 is an electrical block diagram showing one of the subroutines of temperature and time measuring that is performed by the apparatus of the invention.

FIGS. 10 and 11 are schematic block diagrams showing the electronic circuitry of the fertility indicators of FIGS. 2, 3, 6, 7, 8 and 9. The circuit of FIG. 11 is provided with a quartz crystal oscillator 100, preferably having a 1 mhz output which is fed into a programmable timer 101 and a microprocessor 102. The programable timer which interrupts microprocessor 102 performs the clock function needed for the real time temperature measurements. The microprocessor keeps count of the interruptions coming from the programmable timer and thereby keeps track of the precise time. The microprocessor is coupled to input/output interface circuitry 104. Interface circuitry 104 thus allows accessory items, such as keyboard and printer 11 to be fed into the microprocessor. A random access memory (RAM) is also connected to interface circuitry 104. RAM 103 basically stores the daily temperature readings for later readout. Read only memory (ROM) and its programmable versions and/or eraseable programmable versions PROM and EPROM 105 are also connected to interface circuitry and is programmed for fertility indication. Temperature sensor 23 which may consist of a digital temperature sensing device is also connected to interface circuitry 104, so that temperature readings can be digitally fed to microprocessor 102. A clock display 12 and indicator light display 16 are also connected to interface circuitry 104, so that the real time, temperature and indication of the fertility status can be provided. An alarm circuit 106 which sounds audible alarms of variable pitch depending upon the condition of the user is also connected to interface circuitry 104.

Microprocessor 102 is an indefinite variety of logic devices implanted in an intergrated circuit. This integrated circuit is composed of a chip of processed silicon wafer and is usually mounted in a dual in-line package (DIP). The microprocessor can be considered a digital computer. This is because of the similarities of instruction sets, addressing modes and execution speeds between microprocessors and computers. The available microprocessors are manufactured by Intel Corporation (8080) and National Semiconductor Corporation (SC/MP, 8080, and IMP/16).

The computer memory consists of an array of bistable elements. The read-only memory (ROM) and random-access memory (RAM) are semiconductor memories which can consist of an array of "gates" which may be conducting or non-conducting. Each of the memory elements is individually addressable, and each represents a single dinary digit. The location where each binary digit is stored can be uniquely addressed, and it is possible to read the state of every binary digit.

In a read-only memory (ROM), it is not possible to change the state of binary digits in memory. The memory is put in when the ROM is manufactured, so that it can be read but not changed.

A programmable read-only memory (PROM) is like a ROM in that the computer cannot change the state of any binary digits but differs in that it can be initially programmed by the user after manufacture. However, once programmed, it becomes like a ROM in that its state is unchangeable.

The eraseable EPROM is like the PROM in that the user can program it after manufacture. It differs from the PROM in that once programmed, it can be erased and programmed again.

The RAM or random-access memory is a read-write memory wherein the binary digits within the memory can be changed as well as read by the computer. RAMs are manufactured by Intel Corporation (2102) or National Semiconductor Corporations (MM 2102-1 or MM 2102-2). The PROM is manufactured by Intel Corporation (3601) or National Semiconductor Corporation (1702A, 5203 and 5203A). The EPROM is also manufactured by Intel Corporation (1702, 1702A and 4702A).

the fertility indicator of the present invention can be programmed in the manner similar to an ordinary computer. There is a system program which tells the fertility indicator how to operate it. The system program is stored in the semiconductor memory in ROM circuit 105, or can be contained in PROM or EPROM if the system program is to be altered. The system program is made up of a number of instructions that are in coded binary form that are understood by the microprocessor, so that the program can tell the microprocessor how to manipulate bits and which address lines to strobe in order to perform the required function. With instructions from the program contained in the ROM 105, microprocessor 102 enables temperature sensor 23 and sensor 23 then feeds the data through interface circuitry 104 into the microprocessor 102. The data is processed by the microprocessor and stored sequentially in memory in RAM 103. A standby rechargeable battery 109 connected to power supply 110 powers the circuit of FIG. 11 and will prevent loss of memory in RAM 103 should the conventional source of power fail. The ROM program storage 105 also includes a subroutine check circuit as shown in FIG. 10.

Its function is to determine whether a time or temperature reading is higher, lower or the same as the previous reading. When the real time on clock 12 equals the set time to take a reading, the alarm will be activated. For temperature measurements, when the temperature of sensor 23 becomes stabilized, the routine check allows the multi-step program to become initiated. The routine check circuit is a fail-safe mechanism for the temperature. It finds out if the temperature of sensor 23 is the same, greater or less than the previous strobe temperature on the electronic thermometer. If the temperature readings are the same for a number of times, then that temperature can be recorded. If it is less than the previous strobe temperature, the routine check circuit will activate the alarm telling the woman that the sensor has been prematurely withdrawn from the body sensing area. If it is greater, then the routine circuit will keep operating until it levels off on a plateau. The routine check circuit serves as a very efficient comparision program to compare whether something is greater, equal to, or less than a previously recorded figure. When the circuit detects that the temperature has become higher, it will turn off the alarm indicating that the woman has put the probe back into her mouth. In any case, if she doesn't put the probe in her mouth for ten minutes, it will shut off the alarm. When it notices that the temperature has become lower than a previous reading, it will turn on the alarm in a different frequency pitch, notifying the woman that she has dropped it out of her mouth. If, when it notices that the temperature has remained the same for a certain unit of time, it will record the temperature and then activate the alarm at another pitch telling her that the temperature has been recorded. Each alarm will be at a different pitch, so that she knows what is happening. The alarm can also be a vocal message.

In FIG. 11, the microprocessor will strobe alarm 106 at different frequencies or audible tones to indicate different states, such as the watch falling out of the woman's mouth. The alarm provides a continuous beep when the temperature is to be taken, and an intermittent beep until it has stabilized and been recorded. When the temperature has been taken and recorded by the microprocessor, the alarm provides a continuous sound indicating that the temperature has been taken and that the temperature sensing device can be removed from body contact. When the sensor is removed from body contact, the continuous signal terminates.

Quartz crystal 100 vibrating at preferably 1 MHZ (or the frequency required by the microprocessor) keeps the basic beat for both the microprocessor 102 and the programmable timer 101. The microprocessor may also have the programmable timer included on the same chip.

Programmable timer 101 interrupts microprocessor 102 every one thousands of a second or whatever interval it is programmed for. Microprocessor 102 keeps count of the interruptions caused by programmmable timer 101 and thereby knows the time. This time data is stored in a RAM 103 by the processor and is constantly updated. With the help of a program stored in ROM 105, microprocessor 102 processes the time in the twelve hour clock system (or twenty-four hour system as an optional program). The program also allows the microprocessor to keep track of the date (month, day of the month, day of the week and the year).

The processor outputs seven segment logic to the interface circuitry 104 and drives the LED display 16.

If the crystal frequency of oscillator 100 is 1 mhz and the programmable timer is programmed to interrupt every and the programmable timer is programmed to interrupt every second, it will count one million oscillations then interrupt microprocessor 102.

The fertility indicator uses a preferred format for temperature sensing. Programmable time 101 interrupts microprocessor 102 every thousandth of a second. Microprocessor 102 counts ten interruptions and strobes LED displays 16. The microprocessor does this by having a counter (counter "10") this is set to ten decrease by one everytime an interruption occurs. When counter "10" reaches zero, microprocessor 102 strobes the display, sets counter "10" to ten and decreases another counter, counter "6000", by one. When counter "6000" reaches zero, microprocessor 102 increments the time stored in RAM 103 by one minute and resets the counter to "6000". At the same time, the microprocessor is in a subroutine called "check" for operation alarm, where it compares the present time with the alarm set time. When the microprocessor notes that the alarm set time is equal to the displayed time, it activates the alarm. The alarm is caused by the microprocessor strobing a speaker every 1000th of a second (or whatever the counter is set for).

Microprocessor 102 then goes to its next sequential instruction in ROM 105 which tells the microprocessor to return to the subroutine "check" but to do it for "operation temperature".

The microprocessor then reads the temperature from sensor 23 and keeps comparing the readings. The microprocessor is programmed so that:

1. If no increase in temperature reading occurs in one minute, increase the sound volume of alarm 106 until ten minutes and then deactivate the alarm.
2. If the temperature reading increases, deactivate the alarm.
3. If the temperature decreases, activate the alarm.
4. If the readings remain the same for one minute, record the reading in RAM memory and reactivate the alarm (with the time recorded as optional in program).
5. Read sensor.
6. (A) If temperature reading decreases, deactivate alarm.
   (B) If temperature does not decrease, go to step 5.
7. Go to time compare routine.

The microprocessor is updating the time throughout the process. To accomplish the 7 step program, there is a list of instructions in the memory.

1. Go into subroutine check for operation time (FIG. 10).
2. If real time equals set time activate alarm with a frequency "A" (by use of FIG. 10); if real time is greater than or less than set time, go to instruction 1.
3. Go into subroutine check (FIG. 10) for operation of temperature.
4. If temperature of reading n+1 is greater than temperature of reading n, deactivate alarm.
5. If temperature of reading n+2Z is less than previous temperature of reading n+2Z−1, activate alarm at frequency B.
6. If temperature of step 4 is the same as temperature of step 3 (for 100 cycles in operation check) record temperature in memory.
7. Activate alarm 106 at frequency C.
8. If new temperature is lower, deactivate alarm.
9. Go to instruction 2.

The previous routine was based on patient monitoring. That system is a closed looped system that monitors the patient in order to proceed to the next step. That system proceeds when the patient is ready.

Another possible routine is the following. In this routine the processor proceeds by a timed schedule and does not refer to patient as does the previous routine.

When the time is reached for alarm 106 to sound, microprocessor 102 proceeds in the following order:

1. Activates alarm 106 through interface circuitry 104;
2. Waits 6 seconds;
3. Deactivates alarm;
4. Waits three minutes;
5. Reads temperature and writes it in the next sequential memory address in RAM (and the time can be stored in the following address—this is a programmable option);
6. Activates alarm 106;
7. Waits 4 seconds;
8. Deactivates alarm;
9. Processes data;
10. Microprocessor resumes loop.

To accomplish the 10 step program, there is a list of instructions in the ROM as follows:

1. Convert set time into decimal number 1/P—(increment pointer)
2. Store decimal number equivalent of set time in memory 1/P.
3. Read present time 1/P.
4. Convert present time into decimal number 1/P.
5. Subtract set time from present time 1/P.
6. (A) If not equal to zero—go to step 3.
   (B) If equal to zero—1/P.
7. Activate alarm at pitch A—1/P.
8. Wait 6 seconds—1/P.
9. Deactivate alarm—1/P.
10. Wait three minutes—1/P.
11. Read temperature and write it in next sequential address in RAM—1/P.
12. Activate alarm at pitch B—1/P.
13. Wait 4 seconds—1/P.
13. Wait 4 seconds—1/P.
14. Deactivate alarm—1/P.
15. Processes data by referring to algorithm in memory location in ROM to determine patient status—1/P.
16. Store status in memory location—addressable to display indicator—1/P.
17. Return to Step 3.

While only two formats have been discussed in detail, it is obvious that other formats could be designed for the present system to meet particular needs. For example, the fertility indicator could also be used for animals such as the breeding of horses in measuring the cycle between ovulation and predicting the next ovulation to the horse breeder.

The format could also change in the event that the fertility indicator is used in climates where the ambient temperature is high and within the basel body temperature range. In this case, the alarm would stay on continuously for about 15–20 seconds until the temperature is taken. In high temperature situations the vaginal model or the belt model would probably be preferable since neither of these devices have an alarm but would stabilize their temperatures at a preset time interval when it is assumed that they would be in body contact with the user.

The fertility indicator of the present invention was described as being constructed using available electronic components such as a microprocessor, a RAM, a ROM and alarm circuits, it is also possible that a customized integrated circuit chip such as a VLSI (very large size integrated circuit) can be used.

It may also be possible to use linear or analogue integrated circuits instead of the digital integrated circuits for the fertility indicator. Linear integrated circuits are beginning to show promise as replacements for digital integrated circuits in certain areas.

The printer of the present invention was shown specifically designed for the purpose of recording fertility information over a menstrual cycle. The printer is designed to print out one menstrual cycle at a time starting on the first day and printing the temperature indications for each successive day as the information is fed from the RAM through the microprocessor. The printer is capable of distinguishing the beginning and end of each cycle and storing the date or month of each cycle as it is recorded previously in the RAM. Other conventional printers apart from that shown could also be used to display the stored memory information.

While only a few embodiments of the present invention have been shown and described, it will be obvious to those skilled in the art that many changes and modifications may be made thereunto without departing from the spirit and scope of the invention.

What is claimed is:

1. A fertility indicator for measuring and detecting the changes in body temperature of a human subject over a menstrual cycle, comprising:
   a portable watch housing;
   clock timing means disposed in said housing for generating time-based signals;
   logic means disposed in said housing and connected to said clock timing means, and being responsive to said timebased signals for selecting combinations of said time-based signals, and for indicating the correct present time;
   a temperature sensor mounted on said watch housing and coupled to said logic means for measuring the body temperature of the human subject;
   solid state memory means having coded information command signals, and coupled to said logic means for sequencing said logic means to take a plurality of temperature readings at a preset real time, and to terminate the readings when the temperature has stabilized;
   data storage means for sequentially recording each of the stabilized temperatures that were measured during the menstrual cycle and analyzing the stored sequential temperature readings for determining the status of fertility;
   a plurality of colored lights responsive to said solid state memory means, for indicating the start of the menstrual period, the start of ovulation, and the completion of ovulation, respectively, after a preset time interval;
   display means responsive to said solid state memory means, and said data storage means for indicating the status of fertility of the subject during the menstrual cycle;
   alarm means coupled to said logic means and responsive to said clock timing means for indicating the real time for taking a temperature reading, and for indicating when the temperature has been recorded in said data storage means; and
   algorithm processing means disposed within said solid state memory means, for determining the status of the human subject from the temperatures recorded in said data storage means during the menstrual cycle, and predicting the time of ovulation by a predetermined time interval, measured from the next predicted menstrual period by comparison with the stored temperature record in said data storage means.

2. The fertility indicator as recited in claim 1, wherein said alarm means comprises an alarm circuit having a variable pitch responsive to said solid state memory means, for indicating the time when the subject's temperature is to be taken.

3. The fertility indicator as recited in claim 1, additionally comprising a vaginal probe for containing said logic means, solid state memory means, data storage means and said temperature sensor, a battery power source for powering said logic means and data storage means and an external connection for reading the stored data of said probe.

4. The fertility indicator as recited in claim 3, wherein said probe additionally comprises at least one magnetically responsive reed switch coupled between the power source and said logic means and data storage means, and a container having a magnet so that said logic means and data storage means can be deactivated when the probe is placed in the container adjacent to said magnet.

5. The fertility indicator as recited in claim 1, wherein said portable watch housing comprises a wrist watch for containing said logic means, solid state memory means and data storage means, said wrist watch including a bracelet, wherein said temperature sensor is disposed at the end of one arm of said bracelet.

6. The fertility indicator as recited in claim 1, additionally comprising a substantially flat housing for connection to waist straps for containing and housing said logic means, solid state memory and data storage means, a projection formed in said flat housing for body contact, wherein said temperature sensor is located in said projection.

7. The fertility indicator as recited in claim 1, wherein said logic means is a microprocessor computer, said solid state memory means is a read-only memory, and said data storage means is a read-write memory.

8. The fertility indicator as recited in claim 7 wherein said clock timing means comprises a crystal oscillator for generating timed signals, and a programmable timer for interrupting the microprocessor at timed intervals.

9. The fertility indicator as recited in claim 7 wherein said read-only memory has been programmed so that when the real time reaches the set time for taking a temperature, said alarm will sound at a first frequency pitch, when the temperature of said sensor becomes stabilized at a new higher temperature, said alarm will sound at a second frequency pitch, and the temperature of said probe will be sequentially recorded in said read-write memory.

10. The fertility indicator as recited in claim 7 comprising control means coupled to said microprocessor for setting the correct real time and a preset alarm time, and wherein said read-only memory includes a subroutine circuit for comparing the set time with the real time, and an alarm circuit connected to said subroutine circuit so that when both times are equal, said subroutine will activate said alarm circuit to indicate to the subject that the time for taking the temperature has arrived.

11. The fertility indicator as recited in claim 7 wherein said read-write memory is a random access memory.

12. The fertility indicator as recited in claim 1 additionally comprising a further color light for denoting a malfunction as a fail-safe feature.

13. The fertility indicator as recited in claim 1, wherein said portable watch housing comprises a pendant for containing and housing said logic means, solid state memory means, and said data storage means, said pendant including a projection for containing said temperature sensor.

14. The fertility indicator as recited in claim 1, wherein said portable watch housing comprises a watch having a dial for containing said logic means, solid state memory means and said data storage means, an annular ring surrounding said dial and hinged to said watch, said temperature sensor being disposed in said annular ring diagonally opposite said hinge.

* * * * *